US011027085B2

United States Patent
Grashow (10) Patent No.: US 11,027,085 B2
(45) Date of Patent: Jun. 8, 2021

(54) 3-D PATIENT INTERFACE DEVICE ADJUSTMENT SYSTEM AND METHOD

(71) Applicant: KONINKLIJKE PHILIPS N.V., Eindhoven (NL)

(72) Inventor: Jonathan Sayer Grashow, Cheswick, PA (US)

(73) Assignee: Koninklijke Philips N.V., Eindhoven (NL)

( * ) Notice: Subject to any disclaimer, the term of this patent is extended or adjusted under 35 U.S.C. 154(b) by 941 days.

(21) Appl. No.: 15/105,689

(22) PCT Filed: Dec. 10, 2014

(86) PCT No.: PCT/IB2014/066766
§ 371 (c)(1),
(2) Date: Jun. 17, 2016

(87) PCT Pub. No.: WO2015/092623
PCT Pub. Date: Jun. 25, 2015

(65) Prior Publication Data
US 2016/0354571 A1 Dec. 8, 2016

Related U.S. Application Data

(60) Provisional application No. 61/918,896, filed on Dec. 20, 2013.

(51) Int. Cl.
*A61M 16/06* (2006.01)
*A61M 16/00* (2006.01)
(Continued)

(52) U.S. Cl.
CPC .......... *A61M 16/06* (2013.01); *A61B 5/0064* (2013.01); *A61B 5/1075* (2013.01); *A61B 5/1077* (2013.01); *A61B 5/6803* (2013.01); *A61M 16/021* (2017.08); *A61M 16/0605* (2014.02); *A61M 16/065* (2014.02); *A61M 16/0655* (2014.02); *A61M 16/0683* (2013.01); *A61B 5/4818* (2013.01); *A61M 2016/0661* (2013.01);
(Continued)

(58) Field of Classification Search
None
See application file for complete search history.

(56) References Cited

U.S. PATENT DOCUMENTS

| 8,276,588 | B1 | 10/2012 | Connor |
| 2006/0023228 | A1 | 2/2006 | Geng |

(Continued)

FOREIGN PATENT DOCUMENTS

| EP | 2512572 A1 | 10/2012 |
| WO | WO2011073814 A1 | 6/2011 |

(Continued)

*Primary Examiner* — Michelle M Entezari
(74) *Attorney, Agent, or Firm* — Michael W. Haas (57) ABSTRACT

An electronic apparatus including an adjustment determination unit structured to receive patient interface device information for a patient interface device including one or more adjustable features and a 3-D model of a patient's face, and to calculate adjustment information for the patient interface device corresponding to the patient's face using the patient interface device information and the 3-D model of the patient's face and an output unit structured to output the adjustment information.

14 Claims, 6 Drawing Sheets

(51) Int. Cl.
　　　*A61B 5/00*　　　(2006.01)
　　　*A61B 5/107*　　(2006.01)
(52) U.S. Cl.
　　　CPC .............. *A61M 2205/332* (2013.01); *A61M 2205/3306* (2013.01); *A61M 2205/3317* (2013.01); *A61M 2205/3569* (2013.01); *A61M 2205/3592* (2013.01); *A61M 2205/505* (2013.01); *A61M 2205/583* (2013.01); *A61M 2230/65* (2013.01)

(56) References Cited

U.S. PATENT DOCUMENTS

| | | | |
|---|---|---|---|
| 2008/0078396 A1* | 4/2008 | Janbakhsh | A61M 16/06 128/205.25 |
| 2012/0138061 A1* | 6/2012 | Dravitzki | A61M 16/06 128/205.25 |
| 2012/0199131 A1 | 8/2012 | Sofranko | |
| 2012/0232403 A1* | 9/2012 | Smith | A61B 5/015 600/474 |
| 2014/0373374 A1* | 12/2014 | Znamenskiy | A61B 5/1077 33/512 |
| 2015/0055085 A1* | 2/2015 | Fonte | G06Q 30/0621 351/178 |
| 2015/0151066 A1* | 6/2015 | Chodkowski | A61M 16/06 128/206.24 |
| 2015/0151068 A1* | 6/2015 | Dobrusskin | A61M 16/06 128/202.27 |
| 2015/0265794 A1* | 9/2015 | De Kruyff | A61M 16/06 128/200.23 |
| 2015/0283349 A1* | 10/2015 | McLaren | A61M 16/06 128/206.21 |
| 2017/0361045 A1* | 12/2017 | Fu | A61M 16/024 |

FOREIGN PATENT DOCUMENTS

| | | |
|---|---|---|
| WO | WO2013026091 A1 | 2/2013 |
| WO | WO2013088321 A1 | 6/2013 |

* cited by examiner

3-D PATIENT INTERFACE DEVICE ADJUSTMENT SYSTEM AND METHOD

CROSS-REFERENCE TO RELATED APPLICATIONS

This patent application claims the priority benefit under 35 U.S.C. § 371 of international patent application no. PCT/IB2014/066766, filed Dec. 10, 2014, which claims the priority benefit under 35 U.S.C. § 119(e) of U.S. Provisional Application No. 61/918,896 filed on Dec. 20, 2013, the contents of which are herein incorporated by reference.

BACKGROUND OF THE INVENTION

1. Field of the Invention

The present invention pertains to a patient interface device adjustment system, and, in particular, to a patient interface device adjustment system that employs 3-D models.

2. Description of the Related Art

Obstructive sleep apnea (OSA) is a condition that affects millions of people from around the world. OSA is characterized by disturbances or cessation in breathing during sleep. OSA episodes result from partial or complete blockage of airflow during sleep that lasts at least 10 seconds and often as long as 1 to 2 minutes. In a given night, people with moderate to severe apnea may experience complete or partial breathing disruptions as high as 200-500 per night. Because their sleep is constantly disrupted, they are deprived of the restorative sleep necessary for efficient functioning of body and mind. This sleep disorder has also been linked with hypertension, depression, stroke, cardiac arrhythmias, myocardial infarction and other cardiovascular disorders. OSA also causes excessive tiredness.

Non-invasive ventilation and pressure support therapies involve the placement of a patient interface device, which is typically a nasal or nasal/oral mask, on the face of a patient to interface the ventilator or pressure support system with the airway of the patient so that a flow of breathing gas can be delivered from the pressure/flow generating device to the airway of the patient.

Typically, patient interface devices include a mask shell or frame having a cushion attached to the shell that contacts the surface of the patient. The mask shell and cushion are held in place by a headgear that wraps around the head of the patient. The mask and headgear form the patient interface assembly. A typical headgear includes flexible, adjustable straps that extend from the mask to attach the mask to the patient.

Because patient interface devices are typically worn for an extended period of time, a variety of concerns must be taken into consideration. For example, in providing CPAP to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy. Additionally, an improperly fitted mask can cause red marks or pressure sores on the face of the patient. Another concern is that an improperly fitted patient interface device can include gaps between the patient interface device and the patient that cause unwanted leakage and compromise the seal between the patient interface device and the patient. A properly fitted patient interface device should form a robust seal with the patient that does not break when the patient changes positions or when the patient interface device is subjected to external forces. Thus, it is desirable to properly fit the patient interface device to the patient.

Patient interface devices generally have a number of adjustable features. An example of such an adjustable feature is a forehead pad that is translatable and/or rotatable with respect to the cushion. Other examples are headgear straps with adjustable lengths and a cushion that is translatable and/or rotatable with respect to the mask frame. Part of fitting the patient interface device to the patient involves adjusting the adjustable features.

Caregivers generally have little time to assist the patient with adjusting the patient interface device. In some cases, such as where the patient interface device is shipped directly to the patient, the caregiver does not spend any time with the patient to assist with adjusting the patient interface device. The patient is generally not skilled in optimally adjusting the patient interface device, which can lead to a sub-optimal adjustment that may have air leaks, discomfort, or other undesirable effects of an improperly fitted patient interface device. Even in the case that the caregiver does spend some time with the patient to adjust the patient interface, the caregiver may not provide an optimal adjustment due to a number of factors such as: imprecise or inaccurate feedback from the patient; a caregiver that is inexperienced or unskilled at providing an optimal adjustment; ramping or auto-adjusting machines that may operate at a different pressure than the pressure at which the caregiver assesses the fit of the patient interface device; the caregiver is unable to identify discomfort issues that only manifest themselves after several hour or several days; and the location where the fit of the patient interface device is assessed is different than the patient's bedroom.

SUMMARY OF THE INVENTION

In accordance with aspects of the disclosed concept, an electronic apparatus comprises an adjustment determination unit structured to receive patient interface device information for a patient interface device including one or more adjustable features and a 3-D model of a patient's face, and to calculate adjustment information for the patient interface device corresponding to the patient's face using the patient interface device information and the 3-D model of the patient's face and an output unit structured to output the adjustment information.

According to other aspects of the disclosed concept, a method for adjusting a patient interface device includes creating a 3-D model of a patient's face, creating a 3-D model of a patient interface device including one or more adjustable parts, calculating adjustment information for the patient interface device corresponding to the patient's face using the 3-D model of the patient interface device and the 3-D model of the patient's face, and outputting the adjustment information.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed herein, the terms "processor", "processing unit", and similar terms shall mean a programmable analog and/or digital device that can store, retrieve and process data; a controller; a control circuit; a computer; a workstation; a personal computer; a microprocessor; a microcontroller; a microcomputer; a central processing unit; a mainframe computer; a mini-computer; a server; a networked processor; or any suitable processing device or apparatus.

Figure 1:
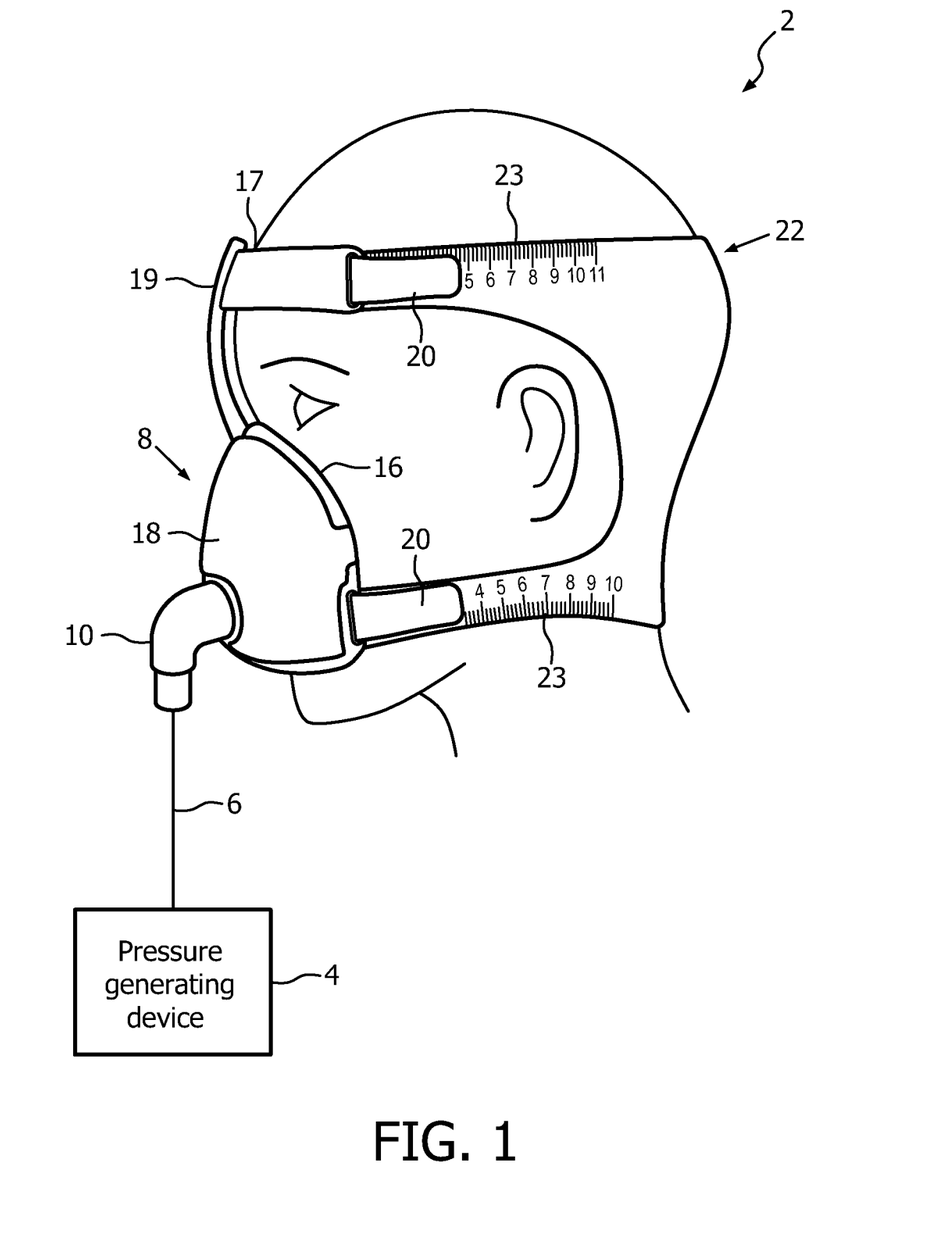
FIG. 1 is a schematic diagram of a system adapted to provide a regimen of respiratory therapy to a patient according to one exemplary embodiment.

A system 2 adapted to provide a regimen of respiratory therapy to a patient according to one exemplary embodiment of the disclosed concept is generally shown in FIG. 1. System 2 includes a pressure generating device 4, a delivery conduit 6, and a patient interface device 8 including an elbow connector 10 fluidly coupled to delivery conduit 6.

Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8.

In the illustrated embodiment, patient interface 8 is a nasal/oral mask structured to cover the nose and mouth of the patient. However, any type of patient interface device 8, such as, without limitation, a nasal mask that covers the patient's nose, a nasal cushion having nasal prongs that are received within the patient's nares, or a full face mask that covers the patient's face, which facilitates the delivery of the flow of breathing gas to, and the removal of a flow of exhalation gas from, the airway of a patient may be used while remaining within the scope of the present disclosed concept. In the embodiment shown in FIG. 1, patient interface device 8 includes a flexible cushion 16 and a rigid or semi-rigid shell 18. An opening in shell 18 to which elbow connector 10 is coupled allows the flow of breathing gas from pressure generating device 4 to be communicated to an interior space defined by shell 18 and cushion 16, and then, to the airway of a patient.

Shell 18 includes a forehead portion 19 and a forehead cushion 17 that is disposed against forehead portion 19 and is structured to contact the patient's forehead area. Cushion 16 and forehead cushion 17 may be adjusted by being translated and/or rotated in order to adjust the fit of patient interface device 8 to the patient.

Straps 20 of a headgear component 22 are attached to shell 18 to secure patient interface device 8 to the patient's head. Straps 20 may be adjusted to tighten or loosen the fit of patient interface device 8 to the patient. Straps 20 and/or headgear component 22 may include indicia 23 (e.g., without limitation, notches; numbers; any other suitable indicia) to indicate different adjustments of straps 20. Indicia 23 are particularly useful in communicating adjustment information to a clinician or patient (e.g., "adjust the forehead strap to 5 and the chin strap to 4"). Although indicia 23 are shown on straps 20 and headgear component 23, it will be appreciated by those having ordinary skill in the art that indicia may also be employed in conjunction with other adjustable features of patient interface device 8 without departing from the scope of the disclosed concept.

Cushion 16, forehead cushion 17, and straps 20 are examples of adjustable features of patient interface device 8. However, it will be appreciated by those having ordinary skill in the art that the disclosed concept is not limited to these adjustable features. It is contemplated that any feature of patient interface device 8 that may be adjusted to change the fit of patient interface device 8 to the patient's face may be considered an adjustable feature of patient interface device 8.

Figure 2:
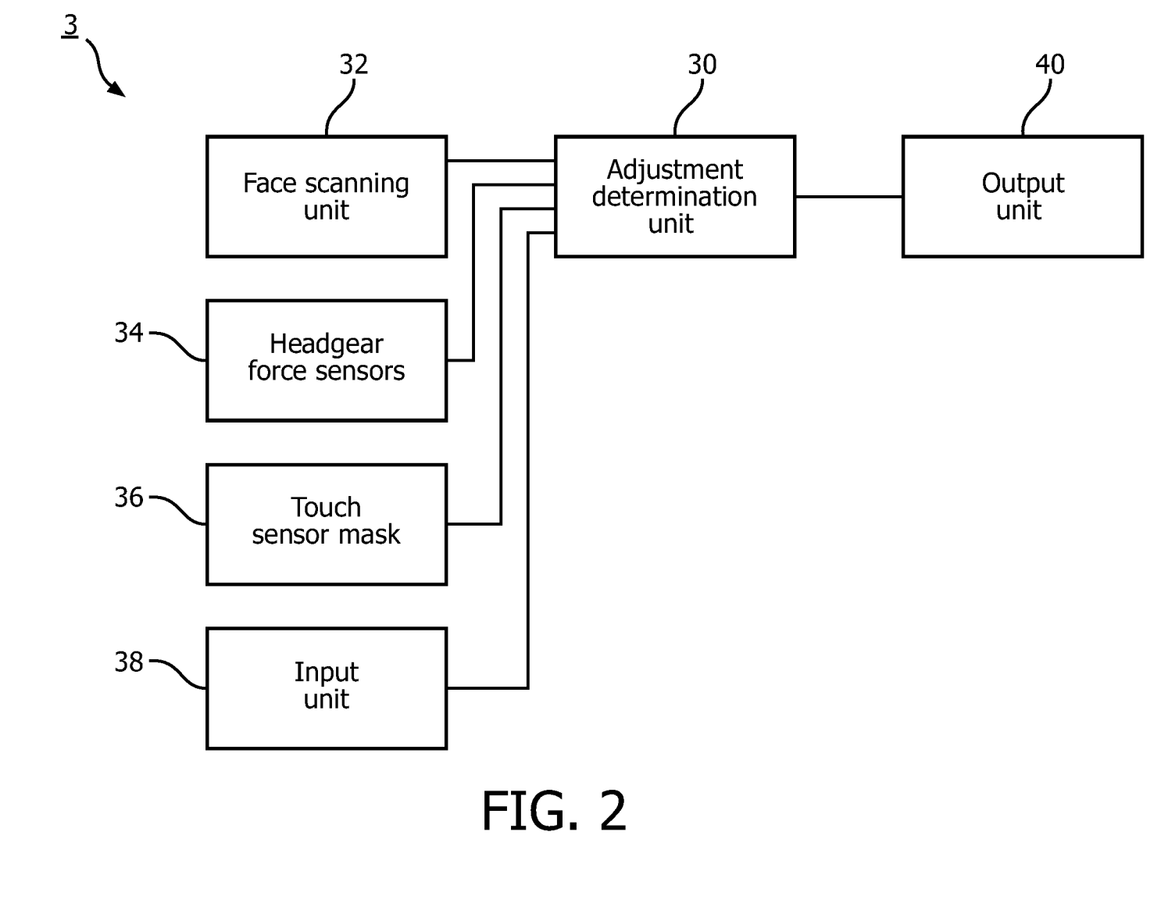
FIG. 2 is a diagram of an electronic apparatus for calculating adjustment information for a patient interface device according to one particular non-limiting embodiment.

An electronic apparatus 3 for determining adjustment information of patient interface device 8 is shown in FIG. 2. The adjustment information is information such as, without limitation, a set of instructions that can be used to adjust the adjustable features of patient interface device 8 in order to provide an optimal fit between patient interface device 8 and the patient. To this end, electronic apparatus 3 includes an adjustment determination unit 30 which will be described in more detail hereinafter.

Adjustment determination unit 30 is structured to receive patient interface device information (e.g., without limitation, a 3-D model of patient interface device 8 or information to identify patient interface device 8) and a 3-D model of the patient's face. Adjustment determination unit 30 uses the patient interface device information and the 3-D model of the patient's face in order to calculate the adjustment information for the adjustable features of patient interface device 8. In one exemplary embodiment, the patient interface device information is a 3-D model of patient interface device 8 and adjustment determination unit 30 uses the 3-D model of patient interface device 8 and the 3-D model of the patient's face to calculate interaction between the patient's face and patient interface device 8 with different settings of the adjustable features. Adjustment determination unit 30 uses these calculated interactions to determine the optimal adjustments for the adjustable features of patient interface device. Interaction between the patient's face and patient interface device 8 may be calculated by performing an analysis such as, without limitation, finite element analysis on the 3-D model of the patient's face and the 3-D model of patient interface device 8. It will be appreciated by those having ordinary skill in the art that any suitable analytic method may be used to calculate the interaction between the patient's face and patient interface device 8 without departing from the scope of the disclosed concept.

In another exemplary embodiment, patient interface device information is identification information for patient interface device (e.g., without limitation, a model number or serial number) and adjustment determination unit 30 is further structured to receive 3-D models of other faces as well as pre-calculated adjustment information for patient interface device 8 corresponding to the other faces. It is contemplated that the pre-calculated adjustment information may be calculated in any suitable manner such as, without limitation, by calculating interaction between 3-D models of other faces and a 3-D model of patient interface device 8. In this exemplary embodiment, adjustment determination unit is structured to compare the 3-D model of the patient's face with the 3-D models of the other faces in order to find one or more of the other faces that are shaped similar to the patient's face. The pre-calculated information for the one or more similar other faces is then used to calculate the adjustment information corresponding to the patient's face. In one exemplary embodiment, the pre-calculated adjustment information for the other face shaped most similar to the patient's face is used as the adjustment information or is modified based on differences between the patient's face and the similar other face and then used as the adjustment information.

In another exemplary embodiment, pre-calculated adjustment information from multiple faces is used to calculate the adjustment information for the patient's face. For example and without limitation, a piece of adjustment information for forehead cushion 17 can be based on one of the other faces having a similarly shaped forehead as the patient and another piece of adjustment information for cushion 16 can be based on one of the other faces having a similarly shaped nose/mouth area as the patient.

It is contemplated that adjustment determination unit 30 may be any type of processing apparatus such as a microprocessor and a memory unit suitable to store and executed software modules. It is also contemplated that adjustment determination unit 30 may be part of pressure generating device 4.

As described above, adjustment determination unit 30 is structured to receive a 3-D model of the patient's face. In an exemplary embodiment of the disclosed concept, electronic apparatus 3 includes a face scanning unit 32 coupled with adjustment determination unit 30. Face scanning unit 32 is structured to create the 3-D model of the patient's face. Face scanning unit 32 may be any device suitable for scanning the patient's face and creating a 3-D model from it. Some examples of suitable devices are, without limitation, optical scanners, cameras, and push-pin arrays. In addition to scanning and creating a 3-D model of the patient's face, face scanning unit 32 may also be capable of scanning and creating a 3-D model of the patient's head and neck. The 3-D model of the patient's head and neck can be useful in determining optimal adjustments for adjustable features such as straps 20, and adjustment determination unit may also use the 3-D model of the patient's head and neck to calculate the adjustment information.

Figure 3:
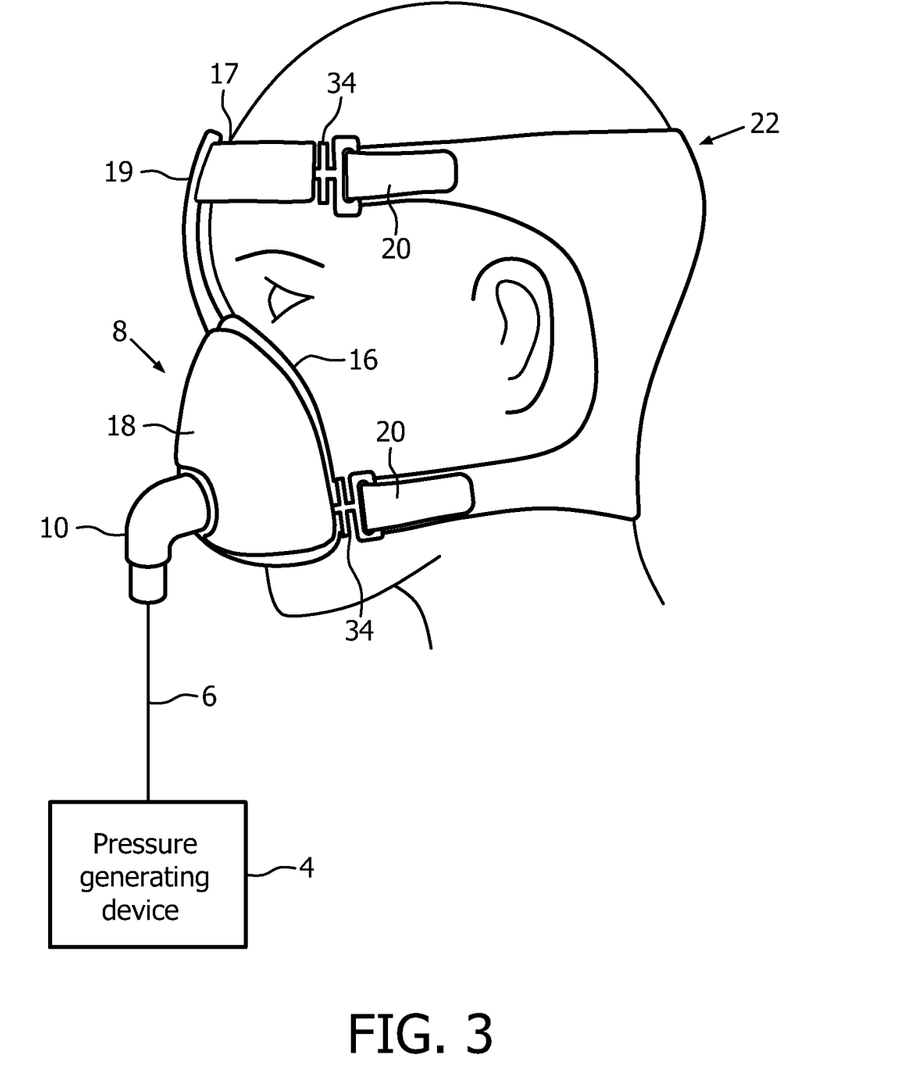
FIG. 3 is a schematic diagram of a patient interface device including headgear force sensors in accordance with one particular non-limiting embodiment.

In some exemplary embodiments, electronic apparatus 3 includes headgear force sensors 34 that are structured to measure force at points in the headgear. Headgear force sensors 34 are used in conjunction with patient interface device 8 as shown in FIG. 3. Continuing to refer to FIG. 3, headgear force sensors 34 are disposed between headgear component 22 and shell 18 so as to be able to measure the force between headgear component 22 and shell 18. If the force between headgear component 22 and shell 18 is too high, for example, straps 20 may be adjusted too tightly and would need to be loosened for a more optimal fit.

Referring back to FIG. 2, headgear sensors 34 are coupled with adjustment determination unit 30. Adjustment determination 30 can then use measurements made by headgear force sensors 34 to calculate the adjustment information. Headgear sensors 34 may be any type of sensor suitable for measuring force. Although headgear sensors 34 are illustrated in FIG. 3 disposed between shell 18 and headgear component 22, it will be appreciated by those having ordinary skill in the art that headgear sensors 34 may be disposed at any suitable location on patient interface device 8. Headgear force sensors 34 may be employed in a patient interface device used for determining adjustment information, and then once the adjustment information is determined, another patient interface device that does not include headgear force sensors 34 is provided to the patient for use.

Figure 4A:
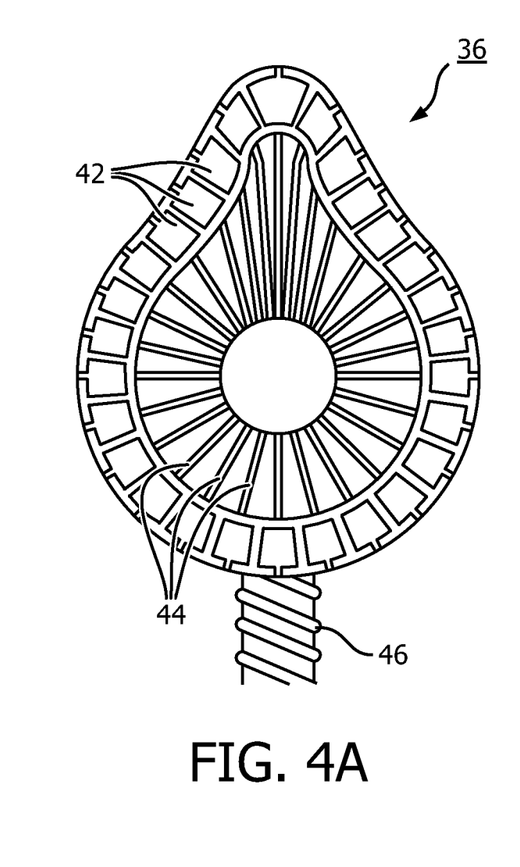
FIGS. 4A and 4B are schematic diagrams of a touch sensor mask in accordance with one particular non-limiting embodiment.
Figure 4B:
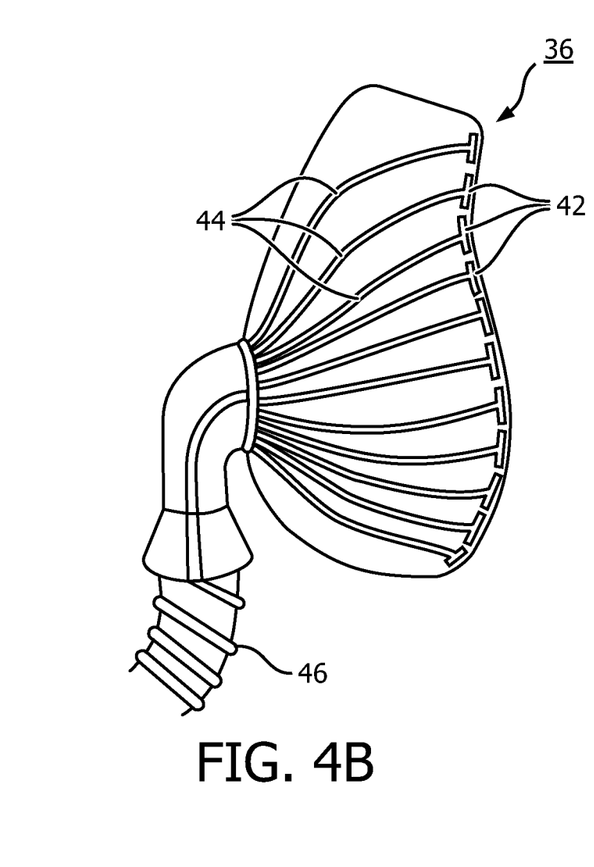

Electronic apparatus 3 may also include a touch sensor mask 36 structured to measure interaction between the patient's face and touch sensor mask 36. Referring to FIGS. 4A and 4B, touch sensor mask 36 includes a number of touch sensors 42 that are structured to contact the patient's face when touch sensor mask 36 is worn. Touch sensors 42 are each coupled to a corresponding electrical lead 44. Electrical lead 44 are coupled to cable connection 46 which communicates the outputs of touch sensors 42 to a connected device such as adjustment determination unit 30. It is also contemplated that outputs of touch sensors 42 may be wirelessly transmitted to adjustment determination unit 30 via a wireless transmitted disposed on touch sensor mask 36, in which case cable connection 46 may be omitted.

Touch sensors 42 may be capacitive touch sensors made of a conductive material such as, without limitation, conductive silicon. Electrical leads may also be made of a conductive material such as, without limitation, conductive silicon, plastic, or metal. Outputs of touch sensors 42 vary based on the amount of contact between them and the patient's face, and their outputs can be useful in determining areas where the mask applies too much force to the patient and areas where it applies too little force to the patient.

Touch sensor mask 36 is shaped substantially similar to a corresponding patient interface device. Once a patient selects the type of patient interface they would like to use, a corresponding touch sensor mask 36, which has substantially the same shape as the selected patient interface device, can then be used to measure interaction between the patient's face and the touch sensor mask 36. Since touch sensor mask 36 is shaped similar to the selected patient interface device, the outputs of touch sensor mask 36 can be used by adjustment determination unit 30 to calculate the adjustment information for the selected patient interface device.

Referring back to FIG. 2, electronic apparatus 38 may also include an input unit 38 coupled to adjustment determination unit 30. Input unit 38 may be any device suitable for inputting information into adjustment determination unit 30 such as, without limitation, a keyboard, a keypad, a mouse, or a touch screen.

Input unit 38 may be used to input additional information for adjustment determination unit 30 to use in calculating the adjustment information. One example of such information is measurements of the patient's head and neck. Another example of such information is the patient's therapy pressure (i.e., the amount of pressure that will be provided to the patient by pressure generating device 4). Also, in some exemplary embodiments, adjustment determination unit 30 is not coupled to one or more of face scanning unit 32, headgear force sensors 34, and touch sensor mask 36, and input unit 38 is used to provide outputs of one or more of these components to adjustment determination unit 30.

Once adjustment determination unit 30 calculates the adjustment information, it provides it to output unit 40 which then outputs the adjustment information 30 to the patient, clinician, or the manufacturer. Output unit 40 may be any suitable device for outputting the adjustment information in a useful manner such as, without limitation, a display, a touch screen display, or a printer. In some exemplary embodiments, the adjustment information is provided to the clinician who adjusts patient interface device 8 for the patient before providing it the patient. In other exemplary embodiments, the adjustment information is provided to the patient and the patient adjusts patient interface device 8 according to the adjustment information. In yet other exemplary embodiments, the adjustment information is provided to a manufacturer that manufactures custom sized adjustable features for patient interface device 8 or adjusts the patient interface prior to shipping to the patient or clinician based on the adjustment information. By using the adjustment information to have the clinician or manufacturer pre-adjust a patient interface device before it is donned by the user, the present invention allows the user to be presented with a patient interface device that is likely to be more quickly fit to that particular user, thus promoting user acceptance and compliance with the positive pressure therapy. In other words, the present invention provides a benefit in that the user receives a patient interface device right out of the box that is already pre-adjusted for their specific facial geometry, without the need for burdensome trial and error on the part of a patient or the clinician. This promotes better initial acceptance of the patient interface device, and improves overall compliance with the therapy.

In some exemplary embodiments of the disclosed concept, adjustment determination unit 30 only uses the 3-D model of patient interface device 8 and the 3-D model of the patient's face to calculate the adjustment information. However, it is contemplated that any additional information or combination of information such as, without limitation, patient therapy pressure, a 3-D model of the patient's head and/or neck, measurements of the patient's head and/or neck, headgear force measurements, and touch sensor mask measurements, can additionally be used to calculate the adjustment information. Using additional information can enhance the accuracy of the adjustment information.

Figure 5:
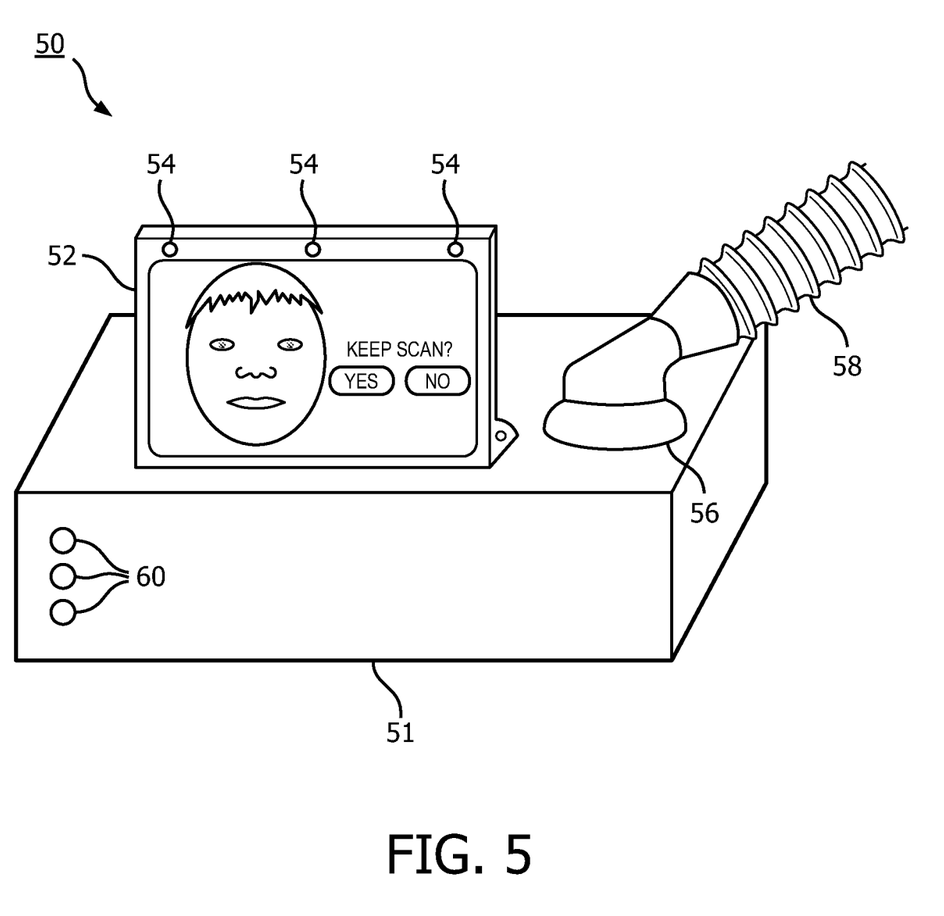
FIG. 5 is a schematic diagram of a system for calculating adjustment information for a patient interface device according to one particular non-limiting embodiment.

An example of an integrated system 50 for determining adjustment information for a patient interface device is shown in FIG. 5. System 50 includes a pressure generating device 51. An adjustment determination unit is included within pressure generating device. A display unit 52 is mounted on pressure generating device 51. Display unit 52 is a touch screen display that can function as both input unit 38 and output unit 40 of FIG. 2. Optical sensors 54 are mounted on display unit 52. System 50 is capable of scanning and creating a 3-D model of a patient's face via optical sensors 54. Pressure generating device 51 is also structured to be coupled with a patient interface device or a touch sensor mask via receptacle 56 and conduit 58. Patient interface device 51 is also structured to be coupled with headgear force sensors via inputs 60. It will be appreciated by those having ordinary skill in the art that system 50 is one exemplary embodiment of the disclosed concept, and the disclosed concept is not limited thereto.

Figure 6:
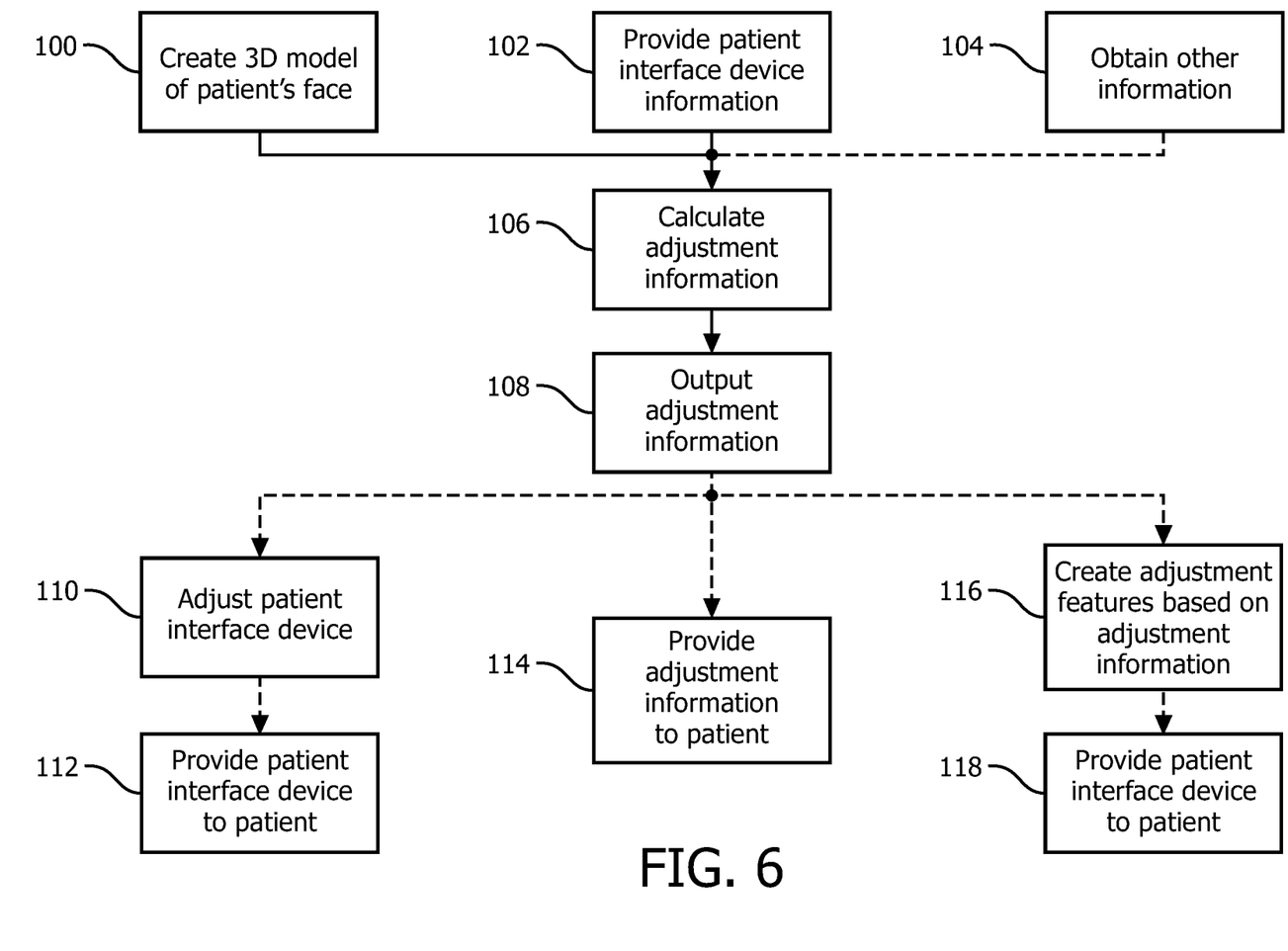
FIG. 6 is a flowchart of a method for calculating adjustment information in accordance with one particular non-limiting embodiment.

A flowchart of a method for determining adjustments for a patient interface device is shown in FIG. 6. It will be appreciated by those having ordinary skill in the art that the method of FIG. 6 may be implemented in part or in whole by electronic apparatus 3 of FIG. 2 or system 50 of FIG. 5. In operation 100 a 3-D model of the patient's face is created and in operation 102 patient interface device information is provided. In operation 104 other information such as, without limitation, patient therapy pressure, a 3-D model of the patient's head and/or neck, measurements of the patient's head and/or neck, headgear force measurements, and touch sensor mask measurements, is obtain. It will be appreciated by those having ordinary skill in the art that operation 104 may be omitted without departing from the scope of the disclosed concept. In operation 106 adjustment information for the patient interface device is calculated and in operation 108 the adjustment information is output.

In operation 110 the patient interface device is adjusted based on the adjustment information, and then, after the patient interface device is adjusted, the adjusted patient interface device is provided to the patient in operation 112. In operation 114, which is an alternative to operations 110 and 112, the adjustment information is provided to the patient. The patient may then adjust the patient interface device on their own. In operations 116 and 118, which form another alternative, adjustable features for the patient interface device are created based on the adjustment information and then the customized patient interface device is provided to the patient.

The present disclosed concept can be embodied in an electronic apparatus, such as, for example and without limitation, a mobile device, a mobile computer, a tablet computer, a peripheral device etc. The present disclosed concept can also be embodied as computer readable codes on a tangible computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, and optical data storage devices.

It is contemplated that any of the embodiments, combination of embodiments, or modification of embodiments of the disclosed concept described herein can be used by, for example and without limitation, a caregiver, technician, or patient in the process of adjusting a patient interface device.

The following is a description of an exemplary embodiment of the present invention. In this embodiment the following steps are performed:
 (a) A 3-D scan is taken of a portion of a patient, such as the patient's head, face, neck, or any combination thereof.
 (b) The patient selects a model or general type of patient interface device from a catalogue.
 (c) The 3-D scan, patient interface device selection, and the patient's therapy pressure are determined using any known technique, and are uploaded to an adjustment determination unit, such as adjustment determination unit 30 illustrated in FIG. 2, which is accessible by the patient interface device manufacturer.
 (d) The adjustment determination unit performs a series of finite element analysis simulations to determine a set of patient interface device adjustments (e.g., adjustment information) that will provide an optimal fit (e.g., robust seal, comfortable, no red marks).
 (e) Before shipping the patient interface device, the patient interface device manufacturer sets the patient interface device adjustments based on the analysis output. For example, as a step in the patient interface device manufacturing and/or packaging process, the adjustable features of the patient interface device are moved to positions determined by the mask fit analysis.

(f) The patient interface device is shipped directly to the patient, and the patient wears the patient interface device without the need for further adjustment.

The following is a description of another exemplary embodiment of the present invention in which an integrated system, such as the integrated system 50 shown in FIG. 5 gives real-time interactive feedback to the patient or clinician to assist the patient interface device fitting process:

(a) A pressure generating device 51 that includes an integrated adjustment determination unit and a patient interface device with force sensors integrated into the headgear straps (see, e.g., FIG. 3) is shipped directly to the patient.

(b) The pressure generating device 51 include a 3-D facial scanner (e.g., optical sensors 54).

(c) The patient is prompted to look at the scanner unit while his or her face is scanned. A display screen shows the resulting scan and the system allows the patient to rescan if necessary.

(d) The adjustment determination unit includes or obtains a database of summary statistics of scanned faces and optimal headgear strapping forces for each of those faces. This database is analysed and a set of optimal headgear strapping forces for the patient is calculated.

(e) The patient puts on the patient interface device and connects it to the pressure generating device 51 via inputs 60.

(f) The adjustment determination unit provides instructions to the patient on how to adjust the straps to achieve an optimal fit based on the forces measured by the headgear strap sensors via display 52.

(g) The adjustment determination unit continually monitors the feedback from the headgear strap force sensors and dynamically updates the fitting instructions as necessary until the optimal headgear strapping forces are achieved.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An electronic apparatus comprising:
   an adjustment determination unit structured to receive patient interface device information for a patient interface device, the patient interface device being structured to facilitate delivery of a flow of gas to an airway of a patient and including one or more adjustable features and a 3-D model of a patient's face, and to calculate adjustment information for the patient interface device corresponding to the patient's face using the patient interface device information and the 3-D model of the patient's face; and
   an output unit structured to output the adjustment information, wherein the adjustment information includes information for adjusting one or more of the adjustable features.

2. The electronic apparatus of claim 1, wherein the adjustment determination unit is further configured to receive a 3-D model of the patient's head and/or neck, and wherein the adjustment determination unit is structured to further use the 3-D model of the patient's head and/or neck to calculate the adjustment information.

3. The electronic apparatus of claim 1, further comprising one or more headgear force sensors structured to measure force between headgear and a shell included in the patient interface device, wherein the adjustment determination unit is structured to receive the headgear force measurement and to further use the headgear force measurements to calculate the adjustment information.

4. The electronic apparatus of claim 1, further comprising a touch sensor mask structured to measure interaction between the patient interface device and the patient's face, wherein the adjustment determination unit is structured to receive the measured interaction and to further use the measured interaction to calculate the adjustment information.

5. The electronic apparatus of claim 1, wherein the patient interface device information includes a 3-D model of the patient's face, and wherein the adjustment determination unit analyzes the interaction between the 3-D model of the patient interface device and the 3-D model of the patient's face to calculate the adjustment information.

6. The electronic apparatus of claim 1, wherein the adjustment determination unit is structured to receive pre-calculated adjustment information for the patient interface device corresponding to other faces, and wherein the adjustment determination unit compares the patient's face with the other faces and uses the pre-calculated adjustment information for the patient interface device corresponding to the one or more other faces determined to be similar to the patient's face to calculate the adjustment information for patient interface device corresponding to the patient's face.

7. The electronic apparatus of claim 1, wherein the output unit is structured to output the adjustment information as a set of instructions for adjusting the patient interface device, and wherein one or more of the adjustable features of the patient interface device include indication markings identifying different adjustment settings.

8. A method implemented on a computer system comprising a non-transitory computer readable medium having computer code stored thereon for adjusting a patient interface device being structured to facilitate delivery of a flow of gas to an airway of a patient and including one or more adjustable features, the method comprising:
   creating a 3-D model of a patient's face;
   providing patient interface device information for the patient interface device;

calculating adjustment information for the patient interface device corresponding to the patient's face using the patient interface device information and the 3-D model of the patient's face; and outputting the adjustment information, wherein the adjustment information includes information for adjusting one or more of the adjustable features.

9. The method of claim 8, further comprising measuring the patient's head and/or neck, wherein calculating the adjustment information further uses the measurements of the patient's head and/or neck.

10. The method of claim 8, wherein the patient interface device information includes a 3-D model of the patient interface device, and wherein calculating the adjustment information includes analyzing interaction between the 3-D model of the patient interface device and the 3-D model of the patient's face.

11. The method of claim 8, further comprising receiving pre-calculated adjustment information for the patient interface device corresponding to other faces, wherein calculating the adjustment information includes comparing the patient's face with the other faces and using the pre-calculated adjustment information for the patient interface device corresponding to one or more of the other faces to calculate the adjustment information for the patient interface device corresponding to the patient's face.

12. The method of claim 8, further comprising using the adjustment information to adjust the adjustable features of the patient interface device prior to providing the patient interface device to the patient; and providing the adjusted patient interface device to the patient.

13. The method of claim 8, further comprising providing the adjustment information to the patient.

14. The method of claim 8, further comprising creating adjustable features based on the adjustment information; and providing the patient interface device including the created adjustable features to the patient.

\* \* \* \* \*